(12) United States Patent
Hamada et al.

(10) Patent No.: US 10,254,213 B2
(45) Date of Patent: Apr. 9, 2019

(54) PARTICLE ANALYSIS APPARATUS

(71) Applicant: HORIBA, Ltd., Kyoto-shi, Kyoto (JP)

(72) Inventors: Motoaki Hamada, Kyoto (JP); Tatsuo Igushi, Kyoto (JP)

(73) Assignee: HORIBA, LTD., Kyoto-shi, Kyoto (JP)

( * ) Notice: Subject to any disclaimer, the term of this patent is extended or adjusted under 35 U.S.C. 154(b) by 0 days.

(21) Appl. No.: 14/800,664

(22) Filed: Jul. 15, 2015

(65) Prior Publication Data

US 2016/0018314 A1 Jan. 21, 2016

(30) Foreign Application Priority Data

Jul. 18, 2014 (JP) .................... 2014-147744

(51) Int. Cl.
| | |
|---|---|
| *G01N 31/22* | (2006.01) |
| *G01N 33/96* | (2006.01) |
| *G01N 15/14* | (2006.01) |
| *G01N 33/49* | (2006.01) |
| *G01J 3/02* | (2006.01) |
| *H01L 33/62* | (2010.01) |
| *G01N 15/10* | (2006.01) |

(52) U.S. Cl.
CPC ..... *G01N 15/1436* (2013.01); *G01N 15/1434* (2013.01); *G01N 15/1459* (2013.01); *G01N 33/49* (2013.01); *G01N 2015/1006* (2013.01); *G01N 2015/1447* (2013.01); *G01N 2015/1486* (2013.01)

(58) Field of Classification Search
USPC ..... 422/73, 82.05, 400; 359/483.01, 484.09; 257/99
See application file for complete search history.

(56) References Cited

U.S. PATENT DOCUMENTS

| | | | |
|---|---|---|---|
| 5,420,444 A | * | 5/1995 | Sawase ................. H01L 27/153 257/465 |
| 5,730,941 A | | 3/1998 | Lefevre et al. |
| 6,813,017 B1 | | 11/2004 | Hoffman et al. |

(Continued)

FOREIGN PATENT DOCUMENTS

| | | |
|---|---|---|
| CN | 1153300 A | 7/1997 |
| CN | 101118208 A | 2/2008 |

(Continued)

OTHER PUBLICATIONS

European Patent Office, Extended European Search Report Issued in Application No. 15177277.9, dated Nov. 25, 2015, 8 pages.

(Continued)

*Primary Examiner* — Dean Kwak
(74) *Attorney, Agent, or Firm* — Alleman Hall Creasman & Tuttle LLP

(57) ABSTRACT

A particle analysis apparatus for flow cytometry, which contains a flow cell having a flow channel for flowing a sample solution containing particles to be analyzed, a light source device for emitting an irradiation light, an optical system for irradiating the irradiation light on an irradiation segment in the flow channel, and a light receiving device for detecting the light obtained thereby. A light source of the light source device is LED, and an electrode formed on a light extraction surface thereof mainly contains a plurality of electric conductor lines arranged in parallel to each other.

6 Claims, 11 Drawing Sheets

(56) References Cited

U.S. PATENT DOCUMENTS

| | | | |
|---|---|---|---|
| 2004/0086159 A1* | 5/2004 | Lary | G01N 15/1425 382/128 |
| 2005/0156189 A1* | 7/2005 | Deguchi | H01L 33/38 257/103 |
| 2006/0231852 A1* | 10/2006 | Kususe | H01L 24/06 257/99 |
| 2008/0024758 A1 | 1/2008 | Tabata | |
| 2008/0116054 A1* | 5/2008 | Leach | B01D 53/007 204/157.3 |
| 2012/0061711 A1 | 3/2012 | Li et al. | |
| 2012/0078531 A1* | 3/2012 | Lo | G01N 15/1459 702/21 |
| 2013/0050782 A1* | 2/2013 | Heng | G01N 15/1434 358/494 |
| 2013/0242302 A1 | 9/2013 | Seo | |
| 2013/0316395 A1 | 11/2013 | Kinugasa | |
| 2014/0091351 A1* | 4/2014 | Tsai | H01L 33/38 257/99 |
| 2015/0177119 A1* | 6/2015 | Martini | G01N 15/1436 435/5 |
| 2016/0025557 A1* | 1/2016 | Morrell | G01N 21/53 356/442 |
| 2016/0033386 A1* | 2/2016 | Reed | G01N 21/53 356/338 |

FOREIGN PATENT DOCUMENTS

| | | |
|---|---|---|
| CN | 102403431 A | 4/2012 |
| EP | 0650202 A1 | 4/1995 |
| JP | H01277740 A | 11/1989 |
| JP | H07176787 A | 7/1995 |
| JP | H08233737 A | 9/1996 |
| JP | H08327529 A | 12/1996 |
| JP | 2003512616 A | 4/2003 |
| JP | 2008135789 A | 6/2008 |
| JP | 2009246311 A | 10/2009 |
| JP | 201264917 A | 3/2012 |
| JP | 2012222219 A | 11/2012 |
| JP | 2013195208 A | 9/2013 |

OTHER PUBLICATIONS

Japanese Patent Office, Office Action Issued in Application No. 2014147744, dated Apr. 24, 2018, 3 pages.

State Intellectual Property Office of the People's Republic of China, Office Action and Search Report Issued in Application No. 201510408330.9, dated Sep. 30, 2018, 6 pages.

Japanese Patent Office, Office Action Issued in Application No. 2014147744, dated Nov. 27, 2018, 3 pages.

* cited by examiner

Flow Direction

PARTICLE ANALYSIS APPARATUS

FIELD OF THE INVENTION

The present invention relates to a particle analysis apparatus for analyzing particles in a liquid, such as blood cells and the like, based on at least flow cytometry.

BACKGROUND OF THE INVENTION

As a method for optically analyzing blood cells in the blood such as red blood cell, white blood cell, platelet and the like, flow cytometry is known. Flow cytometry is a technique including irradiating a predetermined irradiation light as a beam light focused on blood cells in a sample solution (sample liquid) advancing through a flow channel, and analysis such as distinguishing, counting and the like of the blood cells from the resulting optical characteristics such as light scattering, light absorbance and the like (e.g., JP-A-H8(1996)-327529).

FIG. 8 is a sectional view of a configuration example of an apparatus for counting blood cells based on flow cytometry. In flow cytometry, as shown in FIG. 8, a sample solution M10 containing blood cells X10 flows through a flow channel 110, and an irradiation light L10 is irradiated from a light source device 200 through an optical system OP10 on a predetermined irradiation segment in the flow channel. Then, various optical characteristics such as the level of light absorption, level of scattering, level of fluorescence and the like, by each blood cell, with respect to a light (hereinafter to be also referred to as "transmitted light" for the sake of explanation) L20 produced when the irradiation light L10 hits blood cells X10, are measured by a light receiving device 300 through an optical system OP20. The size, kind, number, state and the like of the blood cells are identified from the measurement results. In FIG. 8, the optical systems OP10, OP20 are shown by blocks with a dot and dash line. In fact, a necessary number of optical parts such as lens (lenses) and the like are disposed on the optical path. The optical system OP10 on the light source device side contains a mask member (mentioned later) that forms the cross sectional shape (transverse sectional shape) of the irradiation light L10 into a predetermined shape. The mask member is also called a slit depending on the opening shape of the through-hole.

A part containing a flow channel configured to perform flow cytometry is also called a flow cell. The flow cell may be a single tube. In the apparatus of FIG. 8, the upstream side (lower side of the Figure) of a flow channel 110 has a double tube structure, wherein the flow of the sample solution M10 (containing blood cells X10) from an inner tube 120 is surrounded by a sheath flow from an outer tube 130 and enters into the flow channel 110. Due to this configuration, the flow of the sample solution becomes narrower and the blood cells X10 pass through the flow channel 110 one by one in an orderly manner, which permits irradiation of the irradiation light L10 on each blood cell in an irradiation segment. The wall containing the irradiation segment is transparent so that the irradiation light can penetrate the wall.

Furthermore, it may have a triple tube structure by adding an outer tube to the aforementioned double tube structure. In this case, the flow of a sample solution from the inner tube is surrounded by the first sheath flow, and the flow is further surrounded by the second sheath flow, as a result of which a flow with a suppressed turbulence enters into the irradiation segment.

Conventionally, the above-mentioned particle analysis apparatuses use a halogen lamp as a light source (part generating light) of a light source device (device including light source, electronic power supply, wiring circuit, and housing). However, the halogen lamp has a high heating (calorific) value, and has a problem of a deteriorated performance of measurement since it influences the optical system. Also, a light source device using the halogen lamp has a limitation on downsizing due to the size of the lamp itself. Moreover, since the halogen lamp has a comparatively short rating life, the lamp replacement requires time and cost.

When the analysis apparatus is simultaneously equipped with plural optical measurement systems such as fluorescence measurement and the like, the light from the light source device needs to be dispensed to each optical measurement system. Thus, the light quantity is insufficient for each optical measurement system. However, when the output of the halogen lamp is increased to compensate for the shortage of light quantity, the heating value also increases, and an adverse influence on the optical systems becomes more remarkable. In addition, since a cooling structure becomes necessary, downsizing of the optical systems becomes more difficult, and the cost of the apparatus as a whole also becomes problematically high.

To solve the above-mentioned problems of the halogen lamp, the present inventors studied use of a light emitting diode (hereinafter to be also referred to as an LED) as the light source of the light source device. However, when the LED was actually used as the light source of the apparatus for analyzing minute and fine particles (e.g., blood cells) based on flow cytometry, the following problem was newly found, which is specific to flow cytometry requiring irradiation of the light to an extremely small region.

The problem is that accurate measurement results cannot be obtained in flow cytometry, since the length of the irradiation segment in the flow channel is small (generally about 10 μm-1000 μm), when the LED light is focused on such small irradiation segment by the optical system, the electrode formed in the center of the light extraction surface of the LED forms an obstacle and lowers the strength of the irradiation light in the central part. The problem is more concretely explained in the following.

FIG. 9-FIGS. 11($a$) and 11($b$) are schematic showings facilitating understanding of the above-mentioned problem.

In FIG. 9, FIG. 10, the LED 210 is drawn large in size for the sake of explanation, thus showing the electrode 212 formed on the light extraction surface 211 of the LED. In the following, the electrode formed on the light extraction surface 211 is also referred to simply as "electrode". The LED 210 is mounted on a substrate 220, with the light extraction surface 211 facing toward the flow channel. An electric conductor on the substrate 220, and an electric conductor wire for bonding to be connected to the electrode 212 are omitted. While a light L10 emitted from the LED 210 is drawn to be released solely from the light extraction surface 211 for the sake of explanation, it is in fact also released from a side surface of the LED, and sent in the outgoing direction by a reflection plate and the like (not shown).

On the optical path, lens OP110, mask member OP120, and lens OP130 are provided as the optical system OP10 on the light source device side, and a lens OP20 is provided as an optical system on the light receiving device 300 side. In the Figure, while each lens is shown as a block drawn with a dot and dash line for the sake of explanation, it is in fact also released from a side surface of the LED, and sent in the outgoing direction by a reflection plate and the like (not shown). In fact, many lenses such as combination lens wherein plural lenses are layered, and the like, are used as necessary.

The irradiation light L10 emitted from the LED 210 is formed by a through-hole OP121 of the mask member OP120 to have a rectangular cross sectional shape and irradiated onto the irradiation segment of the flow channel 110.

However, due to the presence of an electrode 212, as an obstacle, formed in the center of the light extraction surface of LED 210 as shown in FIG. 10, in the central part of the irradiation light L10 contains a part having low intensity of the light (hereinafter to be also referred to as low intensity part) L10a. In FIG. 10, the low intensity part L10a is hatched for the sake of explanation. The light in the low intensity part L10a has extremely low intensity as compared to that of the surrounding high intensity part (hereinafter to be also referred to as high intensity part), and the light intensity of the low intensity part is 0 unless the surrounding light sneaks in. The low intensity part is present in the center of the irradiation light, as a region having light intensity sharply decreased from that of the surrounding high intensity part.

FIGS. 11(a) and 11(b) show an irradiation light having a cross sectional shape formed by a mask member and irradiation of the shape-formed light on the irradiation segment of a flow channel. As shown in FIG. 11(a), an irradiation light L10 irradiated on a mask member OP120 is formed to have a cross sectional shape corresponding to the opening of the through-hole OP121 such as rectangle and the like. A light having a formed cross sectional shape is released via the optical system and, as shown in FIG. 11(b), irradiated on the irradiation segment e10 of the flow channel.

As clearly shown in FIG. 11(a), the main part of the center of the cross section of the irradiation light cut away by the through-hole OP121 is occupied by the low intensity part L10a, and the surrounding part is the high intensity part L10b. According to the study by the present inventors, the electrode 212 of LED 210 is focused as an image when the cross section of irradiation light L10 is observed near the entrance of the through-hole OP121. When the central part of such irradiation light L10 passes through the mask member, the main part of the center irradiation light L10 to be irradiated on the irradiation segment e10 becomes the low intensity part L10a, as shown in FIG. 11(b). As a result, a difference between the intensity of transmitted light before entry of particles X10 into the irradiation segment e10, and the intensity of transmitted light after entry of particles X10 into the irradiation segment e10 (particularly, the low intensity part L10a in the irradiation segment) becomes small. What particles have passed through the irradiation segment e10 is determined based on the changes in the received light intensity in a light receiving element. As mentioned above, however, changes in the received light intensity become small due to the presence of the low intensity part and accuracy and reliability of the determination are degraded. These are the above-mentioned problems found by the present inventors.

As for the above-mentioned problems caused by an electrode of LED, the present inventors considered utilization of high intensity part L10b on the outer side of the irradiation light L10 shown in FIG. 11(a). However, as shown in FIG. 10, a light emitting layer 213 of LED emits the strongest light from a part just beneath the electrode 212, and the emission intensity becomes weaker as it transversely gets farther from said part. Therefore, it was found that an irradiation light having sufficient intensity and uniform light intensity cannot be provided over the entire opening of the through-hole (i.e., whole irradiation segment) from the high intensity part outside the irradiation light L10. When a large difference exists in the intensity of the irradiation light in the irradiation segment, the accuracy and reliability of particle determination by the light receiving element are degraded, even though an irradiation light with sufficient intensity seems to be provided over the irradiation segment as a whole, similar to the case where the above-mentioned low intensity part is present. This is because the size of particles cannot be determined appropriately since the received light intensity that should be indicated is not shown when the particles enter a region having a low irradiation light intensity, as mentioned above.

The above-mentioned problems of a light source device in flow cytometry possibly occur similarly not only for counting apparatuses and blood cell classifying apparatuses targeting blood cells, but also apparatuses for analyzing various particles by flow cytometry.

The problem of the present invention is to provide a particle analysis apparatus capable of affording an irradiation light with sufficient intensity on the irradiation segment of the flow channel, permitting down-sizing, and further, having a light source capable of providing uniform light irradiation on the irradiation segment.

SUMMARY OF THE INVENTION

The main configuration of the present invention is as follows.

[1] particle analysis apparatus comprising a configuration to analyze particles in a sample solution based at least on flow cytometry, the particle analysis apparatus comprising:
a flow cell having a flow channel for flowing a sample solution comprising particles to be analyzed;
a light source device for emitting an irradiation light for said flow cytometry;
an optical system for irradiating the irradiation light on an irradiation segment in the flow channel; and
a light receiving device for detecting the light obtained by irradiating the irradiation light on the irradiation segment; wherein
the light source device comprises a light emitting diode as a light source, and the electrode formed on a light extraction surface of the light emitting diode mainly comprises a plurality of electric conductor lines arranged in parallel to each other.

[2] The particle analysis apparatus of the above-mentioned [1], wherein the optical system comprises a mask member having a through-hole to form a cross sectional shape of the irradiation light, and
is adjusted to permit only the light of the following (A), from among the lights emitted from the light emitting diode, to pass through the through-hole and be irradiated on the irradiation segment;
a light emitted from between two adjacent electric conductor lines selected from a plurality of electric conductor lines contained in the electrode of the above-mentioned light emitting diode.

[3] The particle analysis apparatus of the above-mentioned [2], wherein the through-hole of the mask member has a rectangular opening shape,
the mask member is arranged such that the direction of the long side of the rectangle is perpendicular to the flow direction of the above-mentioned flow channel, and
the light emitting diode is disposed such that the longitudinal direction of a plurality of electric conductor lines contained in the electrode of the light emitting diode is the same as the direction of the long side of the rectangle.

[4] The particle analysis apparatus of the above-mentioned [2] or [3], wherein a difference between the maximum value and the minimum value of light intensity in the cross section of the light that passes through the through-hole of the mask member is within 10% of the maximum value.

[5] The particle analysis apparatus of any one of the above-mentioned [1]-[4], wherein the particles are blood cells, and the particle analysis includes counting of blood cells.

BRIEF DESCRIPTION OF THE DRAWINGS

FIG. 3(a)-FIG. 3(d) draw only the electric conductor lines of electrodes, and outer shape lines of bonding pad and light extraction surface are omitted.

DETAILED DESCRIPTION OF THE INVENTION

Effect of the Invention

Figure 2A:
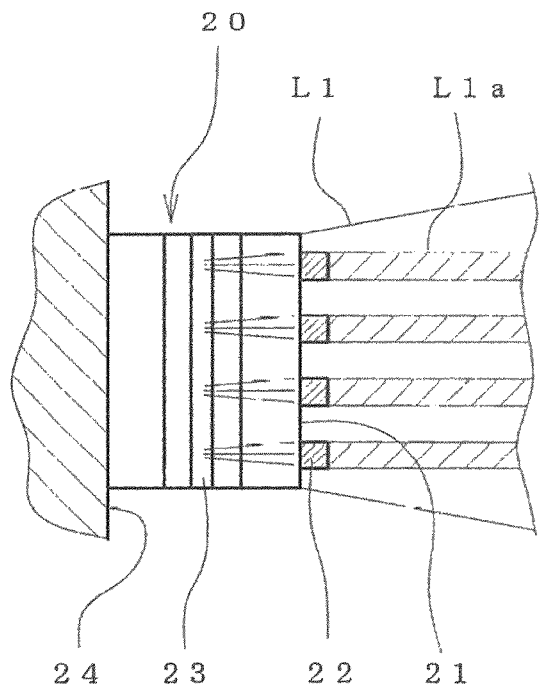
FIGS. 2(a) and 2(b) show, the state of irradiation light emitted from LED, and the state of irradiation light to be irradiated on the irradiation segment in the present invention.
Figure 2B:
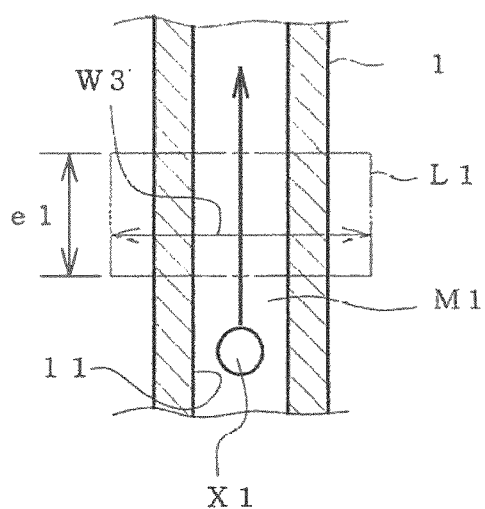
Figure 2C:
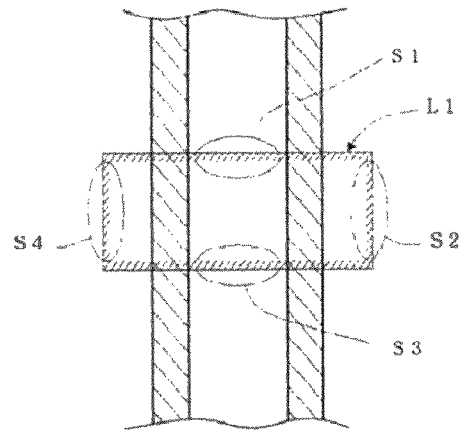
FIG. 2(c) shows, in particular, low intensity parts S1 and S3 of the irradiation light extending perpendicularly to the flow direction, and low intensity parts S2 and S4 of the irradiation light extending in parallel to the flow direction and placed outside of the flow channel, thereby ensuring a uniform light intensity with respect to the width direction of the flow channel.

In the present invention, the LED is used as the light source of the light source device of the particle analysis apparatus instead of the halogen lamp, and the electrode of the LED mainly has a part wherein plural electric conductor lines are arranged in parallel to each other, as represented by a comb-shaped electrode (hereinafter such electrode is to be also referred to as a parallel stripe-shaped electrode). Using the LED having such parallel stripe-shaped electrode as the light source, concentrical existence of the remarkably low intensity part L1a caused by electrode 25 in the main part of the center as shown in FIG. 2(a) which illustrates a light emitted from a light emitting layer 23 and an irradiation light L1 can be avoided, and the preferable irradiation light L1 with the low intensity part dispersed therein can be obtained. As a result, as shown in FIG. 2(b), the irradiation light L1 irradiated on the irradiation segment e1 in the flow channel 11 has a low intensity part preferably dispersed therein. Therefore, even when the LED is used instead of the halogen lamp, degradation of the accuracy and reliability of the determination as mentioned above can be suppressed by using FIG. 9-FIGS. 11(a) and 11(b).

In a preferable embodiment of the present invention, the intensity of the irradiation light to be irradiated on the irradiation segment in the flow channel can be more uniform over the whole irradiation segment. As shown in FIG. 2(a), in the case of the LED having a parallel stripe-shaped electrode, the light released from between adjacent two electric conductor lines contained in the parallel stripe-shaped electrode has an almost uniform intensity over the whole cross section, and has high intensity. This is the characteristics peculiar to the LED having the parallel stripe-shaped electrode. Therefore, by setting the optical system such that only the light released from between two electric conductor lines is selected by the through-hole in the mask member, and using the selected light as the irradiation light, low intensity part produced by the presence of the electrode can be eliminated, the uniform light having the sufficient intensity can be irradiated from the whole cross section of the light (=over the whole irradiation segment). Consequently, even when the LED is used as the light source, the accuracy and reliability of the determination of what particles have passed are not degraded.

The configuration of the particle analysis apparatus according to the present invention is explained in detail in the following by referring to examples.

Figure 1:
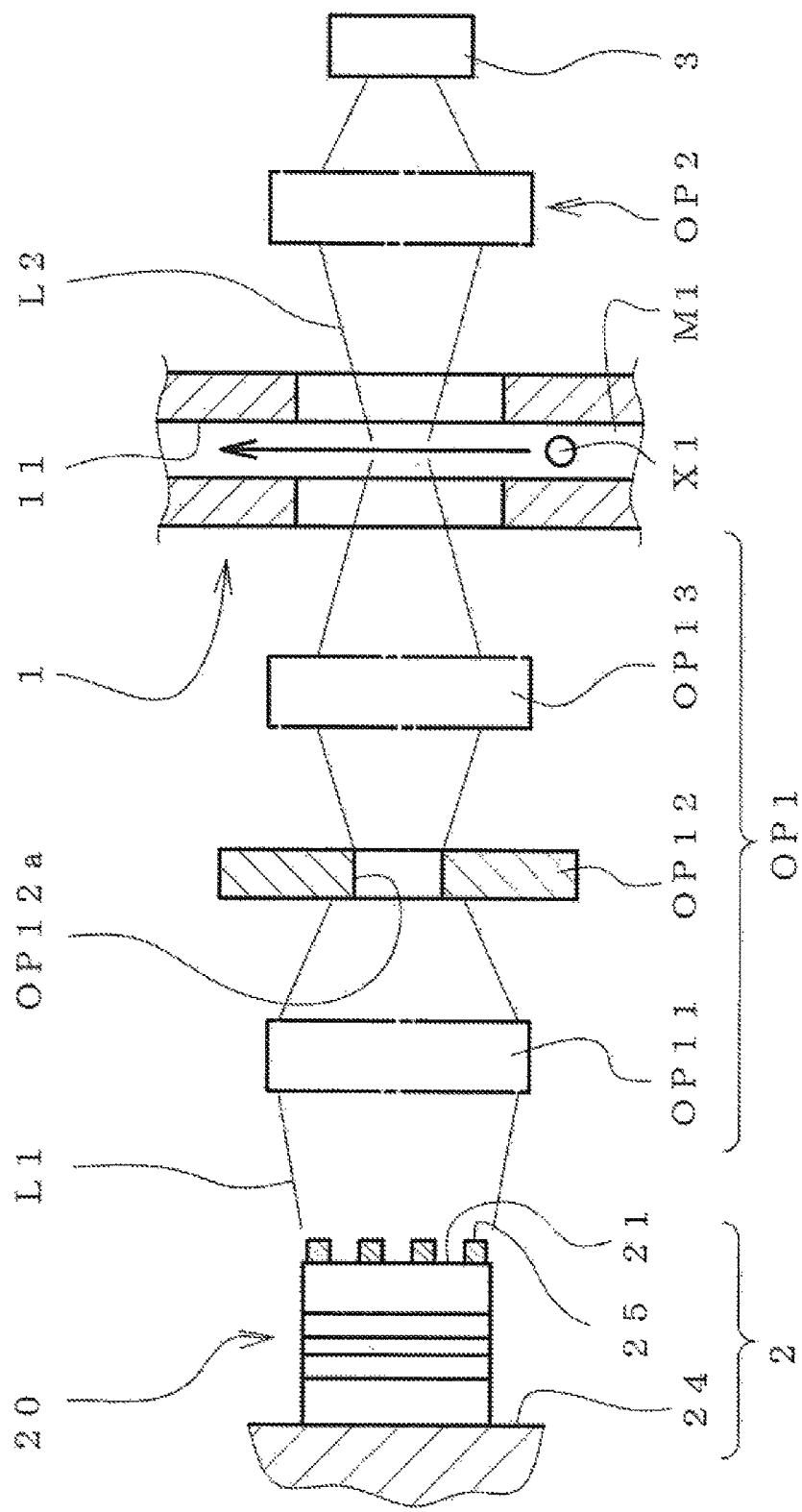
FIG. 1 is a sectional view schematically illustrating an Example configuration of the particle analysis apparatus of the present invention. In this Figure, only a light irradiation part of a flow channel is enlarged, and a detailed structure forming a sheath flow is omitted. Four electrodes of the LED illustrated in this Figure are suggested to have plural parallel electric conductor lines extending perpendicularly to a paper surface of the Figure (also in FIGS. 2(a) and 2(b)). In this Figure, for the sake of explanation, respective lenses constituting optical systems are expressed as blocks shown with a dot and dash line.

The particle analysis apparatus is, as in the example shown in FIG. 1, FIG. 2(a) and FIG. 2(b), an apparatus comprising a configuration to analyze particles in a sample solution based at least on flow cytometry, the particle analysis apparatus comprising a flow cell 1 having a flow channel 11 for flowing a sample solution M1 containing particles X1 to be analyzed; a light source device 2 for emitting an irradiation light L1 for flow cytometry; an optical system OP1 for focusing and irradiating the irradiation light L1 on an irradiation segment e1 in the aforementioned flow channel 11 (FIG. 2(b)); and a light receiving device 3 for detecting the light (transmitted light) L2 obtained by irradiating the irradiation light L1 on the irradiation segment e1. In the embodiment of FIG. 1, an optical system OP2 is provided on the light receiving device side.

The most important aspect of the present invention resides in a light source device 2. In addition, the optical system OP1 (particularly mask member OP12) adjusted to utilize the characteristics of the light source device is also important.

As shown in FIG. 1, FIG. 2(a) and FIG. 2(b), the present invention uses LED 20 as a light source of a light source device 2, and electrode 25 formed on the light extraction surface 21 of the LED is a parallel stripe-shaped electrode typically represented by comb-shaped electrodes. Using an LED provided with such electrode as a light source, as mentioned above, the problems explained by referring to FIG. 9-FIGS. 11(a) and 11(b) can be solved.

The prior art can be referred to as for the basic configuration of each part of the apparatus used to perform flow cytometry, for example, flow cell, optical system, light receiving device, configuration of control circuit, analysis method by a processor (computer and the like), and the like.

Figure 9:
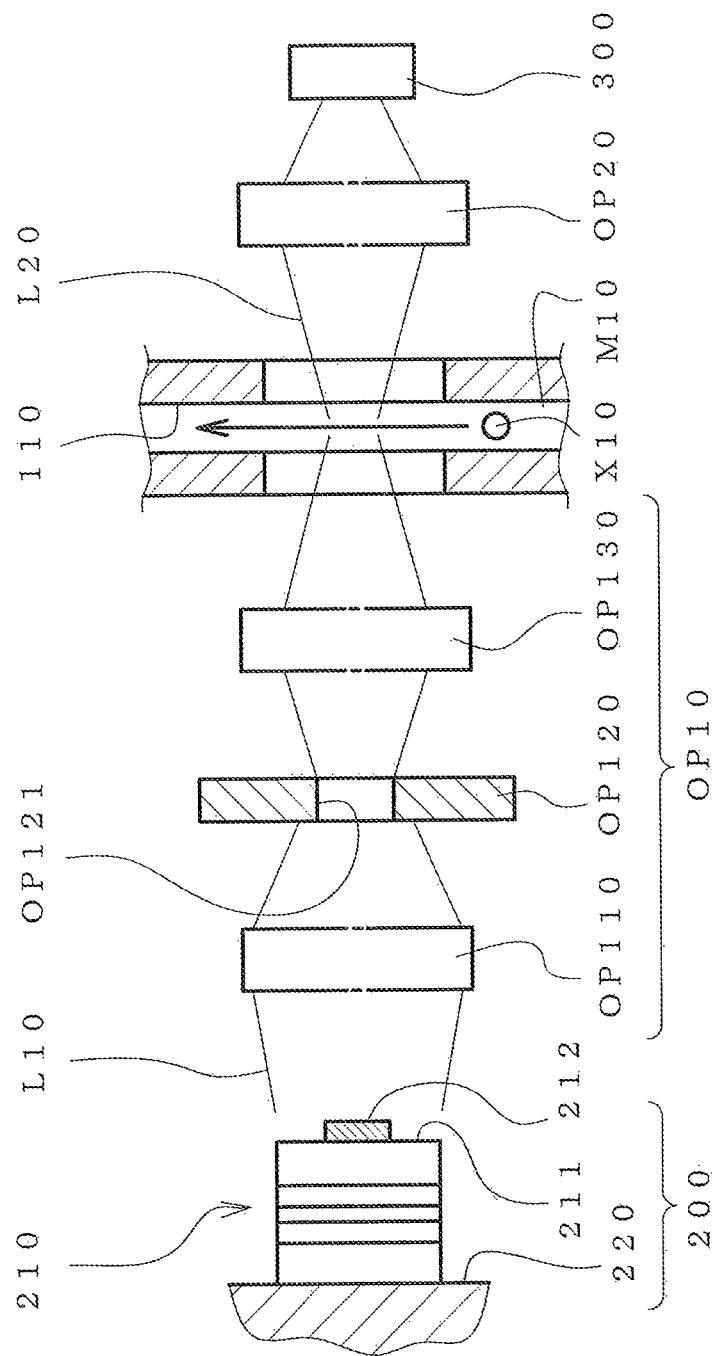
FIG. 9 is a sectional Figure showing the problem of LED used as the light source in the conventional particle analysis apparatus. In this Figure, each lens constituting an optical system is expressed as a block shown with a dot and dash line, as in FIG. 1.
Figure 10:
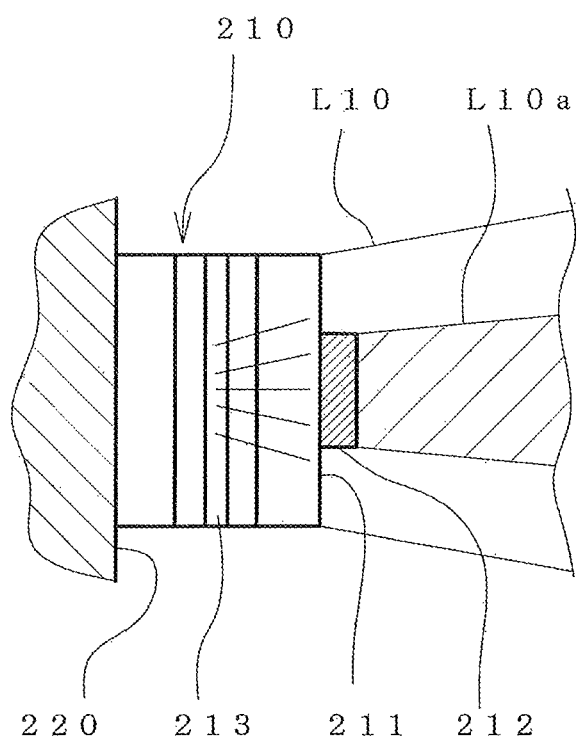
FIG. 10 is a sectional Figure showing the problem of LED used as the light source in the conventional particle analysis apparatus, wherein LED is enlarged.
Figure 11A:
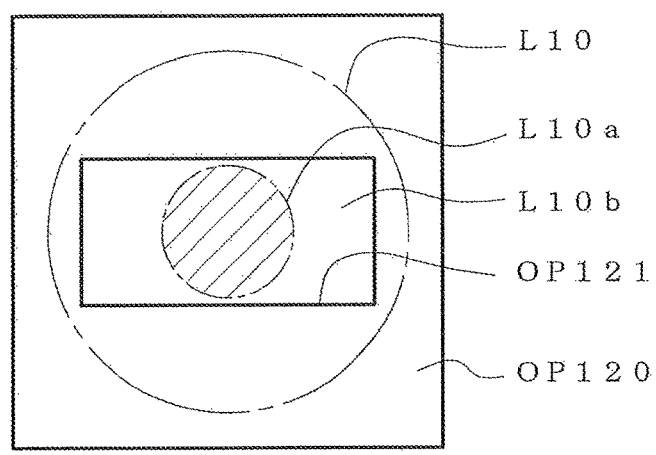
FIGS. 11(a) and 11(b) are sectional Figures showing the problem of LED used as the light source in the conventional particle analysis apparatus, including formation of a cross sectional shape of the irradiation light by a mask member, and irradiation of the shape-formed light on the irradiation segment in the flow channel.
Figure 11B:
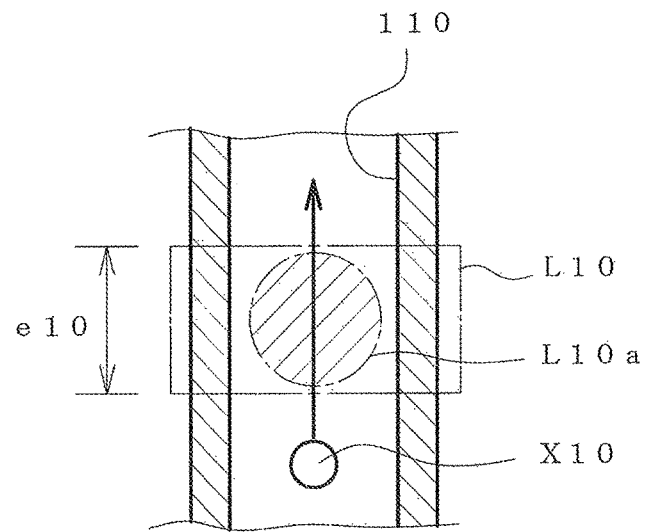

In the example of FIG. 1, like FIG. 9, LED 20 is mounted on a substrate 24, and a light extraction surface 21 is directed toward a flow channel 11 of a flow cell 1. On the optical path are formed, as the optical system OP1 on the light source device 2 side, lens OP11, mask member OP12, and lens OP13, and a lens OP2 as the optical system on the light receiving device 3 side. The irradiation light L1 emitted from LED 20 has a cross sectional shape (a shape of cross section (transverse section) when cut perpendicularly to the optical axis), which is formed according to the shape of an opening of a through-hole OP12 of the mask member OP12, and the light is irradiated on the irradiation segment of the flow channel 11 via lens OP13. In FIG. 1, while each lens is shown as a block drawn by a dot and dash line for the sake of explanation, in fact, many lenses such as combination lens wherein plural lenses are layered, and the like, are used as necessary. The flow cell 1 has a wall which is partially or entirely transparent, so that irradiation light can be irradiated on the irradiation segment of the flow channel.

While the emission wavelength of the LED used as the light source in the present invention is not particularly limited, a wavelength of about 200 nm-2500 nm is preferable, and about 400 nm-800 nm is more preferable, to replace the halogen lamp.

Examples of the LED having such emission wavelength include one having a semiconductor material such as AlGaAs, GaP, GaAsP, AlGaInP, InGaN, ZnSe and the like at least as a material of a light emitting layer. In such LED, the light extraction surface is often a surface of p-type layer side.

While the light emitting output of the LED to be used in the present invention is not particularly limited, one showing a light emitting output of about 100 mW or more is preferable.

An electrode of the LED used as the light source in the present invention is not particularly limited as for the position of electric conductor lines that connect parallel electric conductor lines 22, and the shape drawn by the electric conductor lines as a whole, as long as it mainly has a part wherein plural electric conductor lines are arranged and disposed in parallel to each other, as in the typical patterns shown in FIGS. 3(a)-3(d).

Figure 3A:
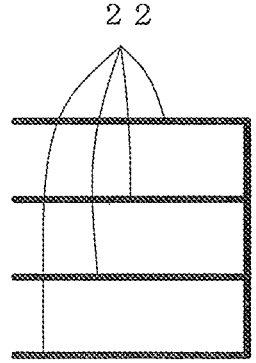
FIGS. 3(a)-3(d) show preferable forms of the electrodes of LED utilizable in the present invention.
Figure 3B:
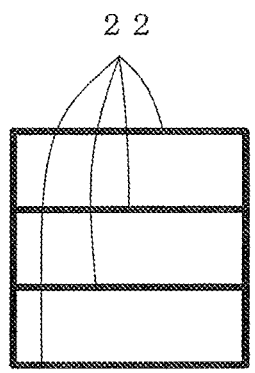
Figure 3C:
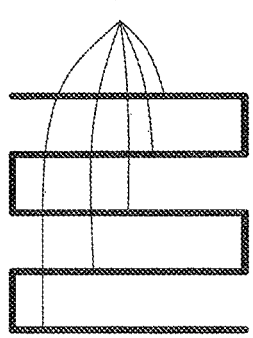
Figure 3D:
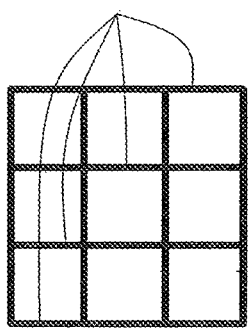

FIG. 3(a) is a comb-shape. FIG. 3(b) is a square shape formed by adding a vertical electric conductor line to the comb-shape of FIG. 3(a) to close the outer circumference. FIG. 3(c) is a meandering-shape. FIG. 3(d) is a net-shape. In addition, these shapes may be combined. FIGS. 3(a)-3(d) are explanation figures and do not limit the number of parallel electric conductor lines 22.

In the net-shape of FIG. 3(d), the electric conductor lines divide the light extraction surface more finely than in the embodiment of FIG. 3(a)-FIG. 3(c). However, this embodiment is utilizable depending on the size of the LED chip and emission intensity, and the effect of the present invention can be afforded.

In all of the embodiments of FIG. 3(a)-FIG. 3(d), a bonding pad (not shown) is formed on the periphery or corner of the extraction surface to avoid being an obstacle to the extraction of light.

Figure 4:
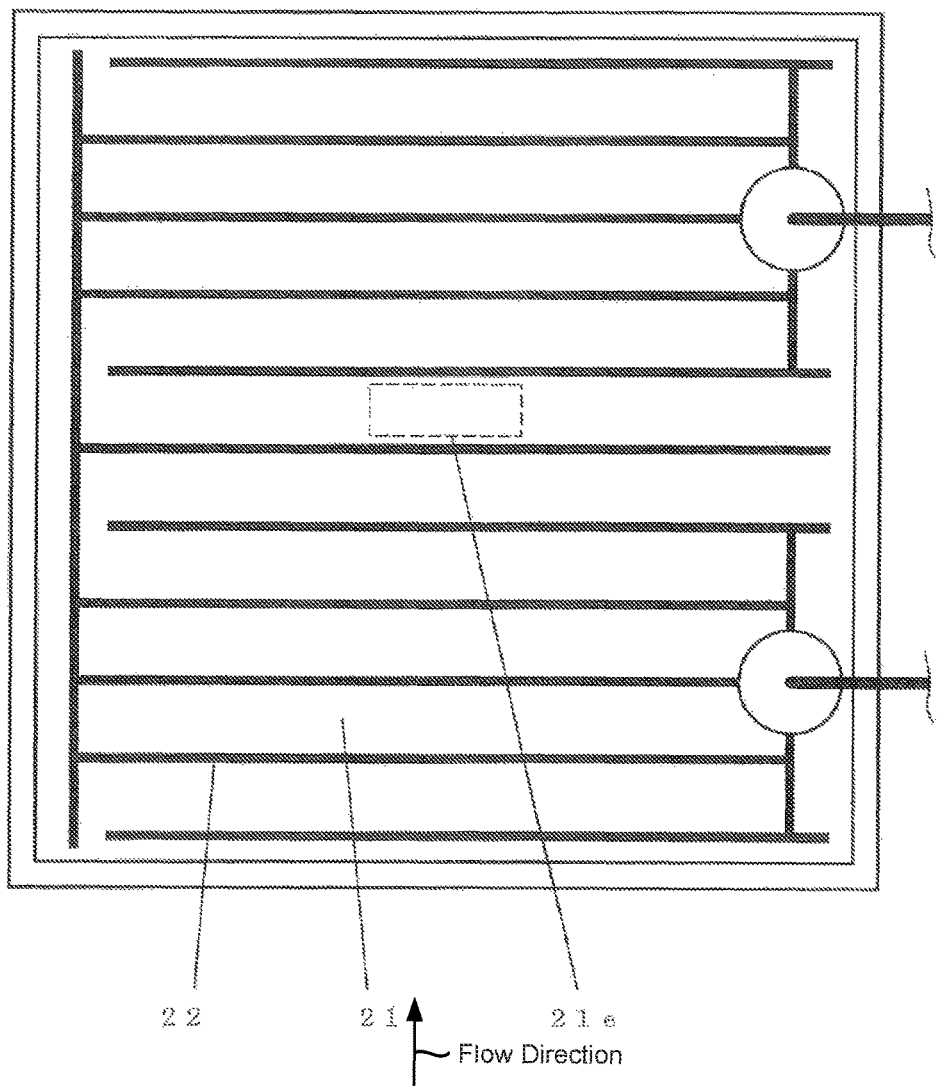
FIG. 4 is a schematic showing of the light extraction surface of LED utilizable in the present invention, and shows preferable one embodiment of the electrode. In this Figure, electric conductor lines (symbol 22) of the electrode are shown with a thick line.

FIG. 4 shows one preferable embodiment of the shape of an electrode of the LED. In this Figure, the whole light extraction surface of LED is shown, and eleven parallel electric conductor lines 22 are arranged in the center of the extraction surface 21. The electric conductor lines 22 are connected to each other at one end part or both end parts, and form a complicated shape as a whole such as the shape formed by FIG. 3(a) and FIG. 3(b) in combination. In the embodiment of FIG. 4, a circular bonding pad is formed at two right ends of the square extraction surface 21, and an outside conductor wire is connected to each of them.

Figure 5:
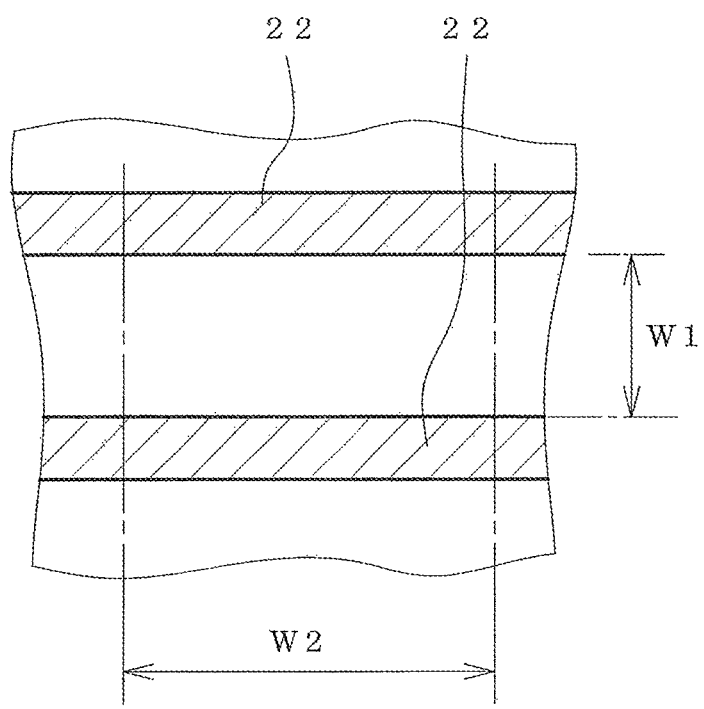
FIG. 5 explains preferable size of the electrode of LED, which is utilizable in the present invention.

FIG. 5 is a partially enlarged view showing two adjacent electric conductor lines 22 in the electric conductor lines constituting the electrode of the LED. The distance (width of exposed part of light extraction surface) W1 between electric conductor lines 22 varies depending on the size of the LED, and is preferably about 10 μm-1 mm. The length (continuous length of exposed part of light extraction surface) of the electric conductor lines 22 is preferably not less than about 10 μm, more preferably not less than 1 mm. The upper limit of W2 varies depending on the size of the LED.

The mask member OP12 contained in the optical system OP1 on the light source device side has the through-hole OP12a having the opening having a shape for forming the cross sectional shape of the irradiation light L1, and only the irradiation light that passed through the through-hole later passes through the optical system and is irradiated on the irradiation segment of the above-mentioned flow channel.

The shape of the opening of the through-hole can be determined according to the width of the flow channel and the length of the irradiation segment. Since the irradiation segment is defined in the flow channel by two parallel straight lines, a square and a rectangle are preferable shapes. The irradiation light that passed through the through-hole is later irradiated on the irradiation segment in the flow channel by the optical system. In this case, the mask member is positioned such that the parallel two sides of the cross sectional shape (square or rectangle) of the irradiation light are perpendicular to the flow direction of the flow channel. The length of the aforementioned two sides perpendicular to the flow direction of the flow channel is preferably determined to be longer by a suitable margin than the width of the flow channel. Such margin facilitates positioning of the irradiation light relative to the direction perpendicular to the flow channel.

When the shape of the opening of the through-hole is square or rectangle, the ratio of the length of the two perpendicular sides of the through-hole can be appropriately determined according to the ratio of [flow channel width+ positioning margin] and [length of irradiation segment in flow channel]. The square and rectangle may have a round corner as long as it does not influence irradiation and positioning.

In the flow cell for the analysis of blood cells, as shown in FIG. 2(b), since [length of irradiation segment e1 in flow channel] is often shorter than [flow channel width+positioning margin] W3, the shape of the opening of the through-hole often becomes a rectangle. When the irradiation segment e1 in the flow channel is set longer, the shape of the opening of the through-hole becomes closer to square, and becomes a rectangle longer in the flow direction.

When the shape of the opening of the through-hole is a rectangle and the mask member OP12 is configured such that the long side of the rectangle is perpendicular to the flow direction of the flow channel, as shown in FIG. 2(b), the length of the short side of the cross sectional shape (rectangle) of an irradiation light L1 irradiated on the flow channel is the length of the irradiation segment e1. On the other hand, as mentioned above, the length W3 of the long side of the cross sectional shape (rectangle) of the irradiation light L1 irradiated on the flow channel is preferably set longer than the width of the flow channel.

Figure 6A:
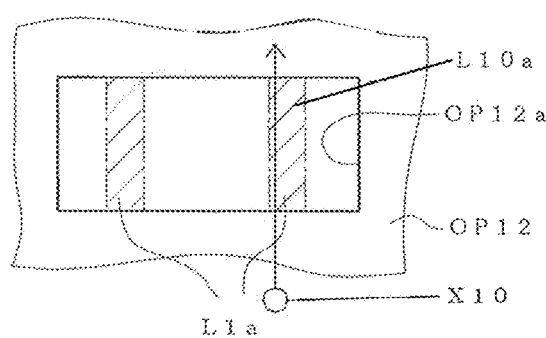
FIGS. 6(a) and 6(b) show the relationship between the low intensity part of the irradiation light and the through-hole of the mask member in the present invention.
Figure 6A:
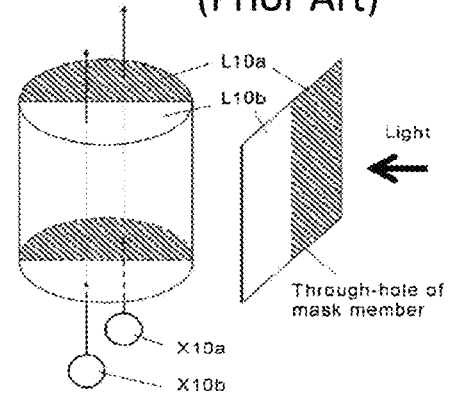
Figure 6B:
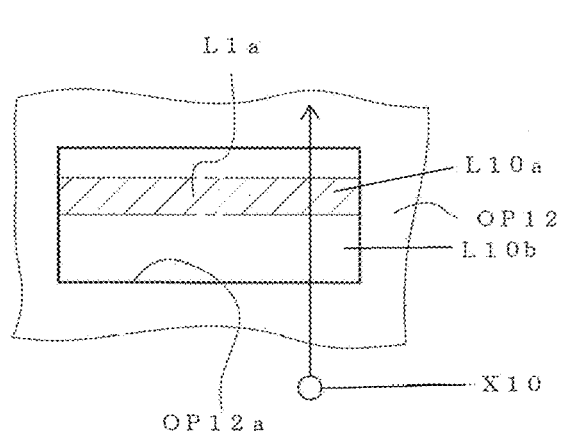
Figure 6B:
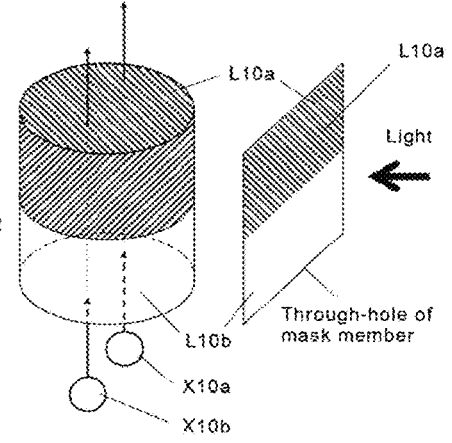

FIGS. 6(a) and 6(b) show the state of the low intensity part when the light emitted from the LED having the parallel stripe-shaped electrode passes through the through-hole of the mask member. While the shape of the opening of the through-hole may be square, in the embodiment of FIGS. 6(a) and 6(b), it is a rectangle. In the embodiment of FIG. 6(a), the low intensity part L1a caused by the parallel stripe-shaped electrode extends in parallel with the short side of the through-hole OP12a such that particle X10a passes through low intensity part L10a alone, particle X10b passes through high intensity part L10b alone, and the intensities of the light irradiating the particles X10a and X10b are vastly different. On the other hand, in the embodiment of FIG. 6(b), the low intensity part L1a extends in parallel with the long side of the through-hole OP12a, such that both particle X10a and particle X10b pass through both the low intensity part L10a and the high intensity part L10b of the irradiation light, and regardless of where the particles pass through the cross section perpendicular to the flow, the intensities of the light irradiating the particles X10a and X10b are not significantly different. In any embodiment, while the problem explained using FIG. 9-FIGS. 11(a) and 11(b) is reduced, since the low intensity part L1a is contained in the irradiation light passing through the through-hole, an adverse influence on the measurement remains.

In a more preferable embodiment of the present invention, therefore, the optical system is adjusted such that only [a light emitted from between two adjacent electric conductor lines selected from the plurality of electric conductor lines contained in the parallel stripe-shaped electrode], from among the lights emitted from LED having a parallel stripe-shaped electrode, would pass through the through-hole. Adjusting the optical system in this context is an operation of, for example, selection of the size of the through-hole, selection of necessary lens (lenses), determination of the positions of mask member and lens, adjustment of the focusing point and optical path, and the like, and these operations may be combined as appropriate.

In this embodiment, the irradiation light after passing the through-hole does not have the low intensity part, and the intensity of the irradiation light in the irradiation segment becomes uniform. Therefore, the degradation of the accuracy and reliability of the determination of particles can be sufficiently suppressed even when the LED is used as the light source.

Figure 7A:
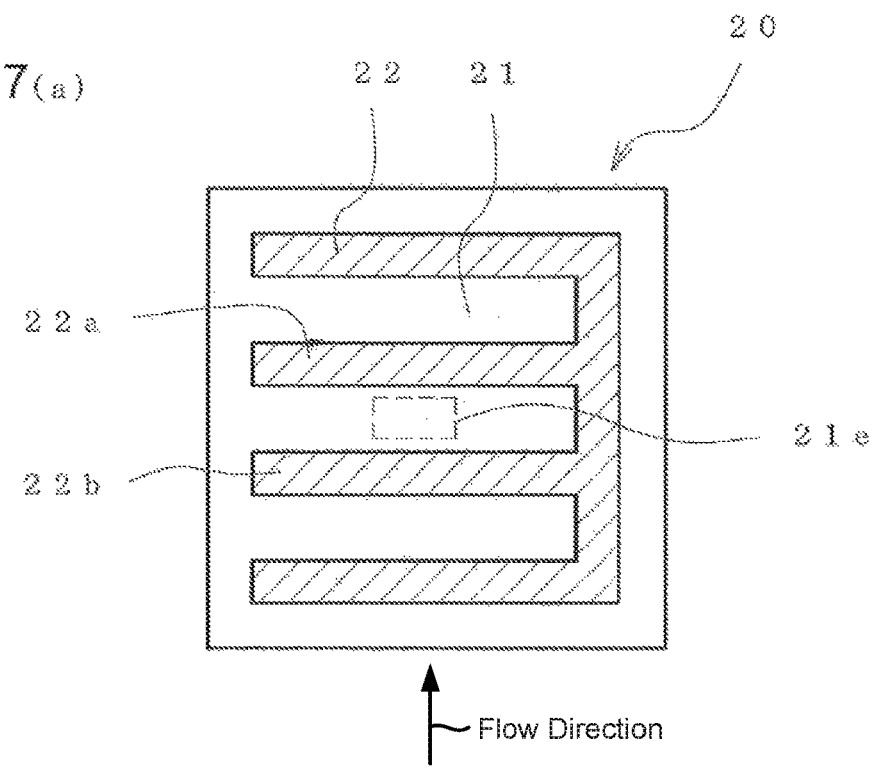
FIGS. 7(a) and 7(b) show the relationship between the low intensity part of the irradiation light and the through-hole of the mask member in a preferable embodiment of the present invention.
Figure 7B:
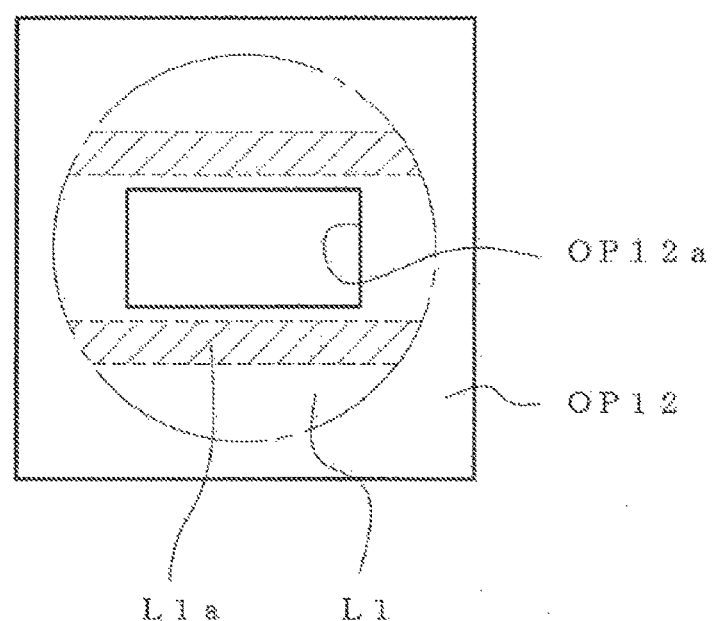
Figure 8:
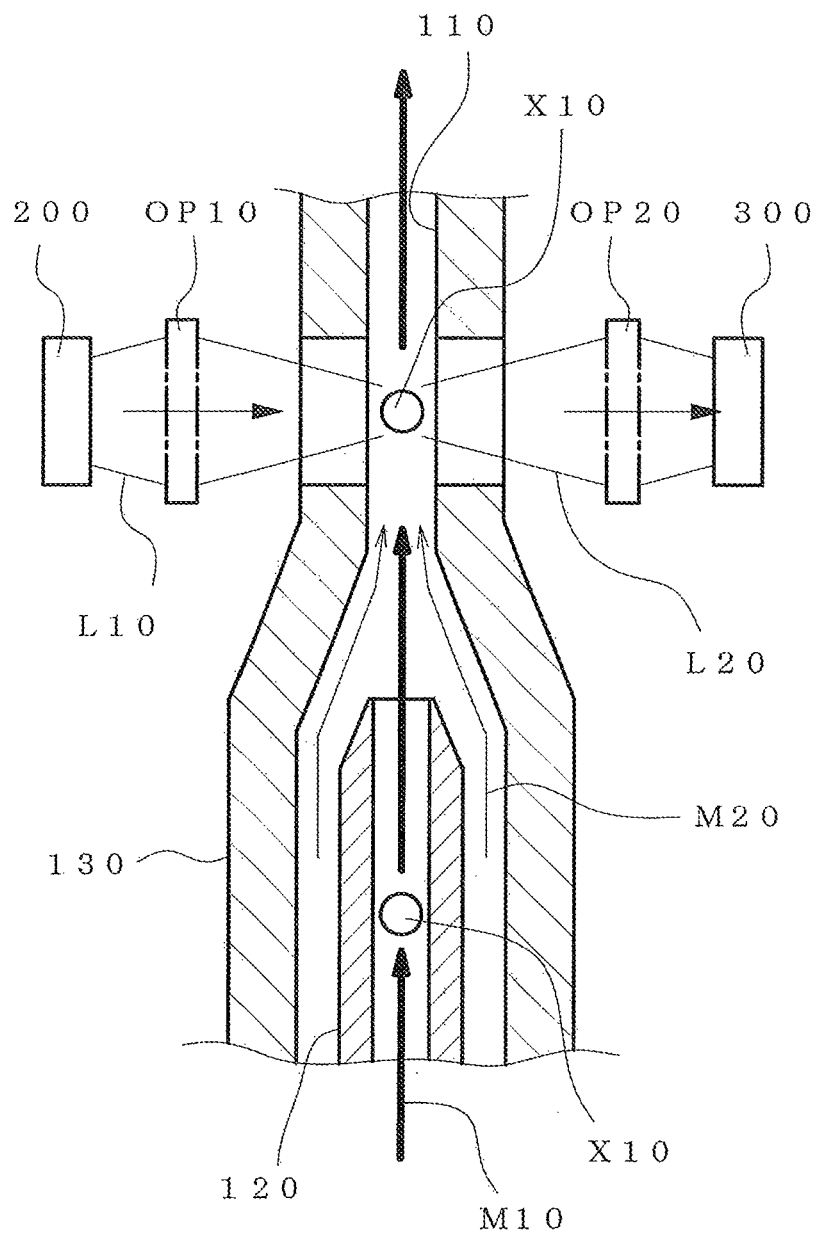
FIG. 8 is a sectional view showing a configuration example of the conventional particle analysis apparatus for flow cytometry.

FIGS. 7(a) and 7(b) show a preferable embodiment when only [a light emitted from between two adjacent electric conductor lines selected from the plurality of electric conductor lines contained in the parallel stripe-shaped electrode] is passed through the through-hole of the mask member. In FIGS. 7(a) and 7(b), for the sake of explanation, a comb-shaped electrode is used as the parallel stripe-shaped electrode. While the shape of the opening of the through-hole is rectangle that corresponds to the area between two adjacent electric conductor lines to sufficiently utilize said area, it may be square.

The through-hole of the mask member is, as mentioned above, arranged to have one side thereof (long side in FIGS. 7(a) and 7(b)) perpendicular to the flow direction of the above-mentioned flow channel. The LED is disposed such that the longitudinal direction of the electric conductor lines 22 contained in the comb-shaped electrode is the same as the direction of one side of the through-hole (long side in the example of FIGS. 7(a) and 7(b)). As shown in FIG. 7(a), the optical system is adjusted such that only the light emitted from a region 21e in between two electric conductor lines 22a, 22b adjacent to each other, which are selected from the parallel electric conductor lines 22 of the comb-shaped electrode, will pass through the through-hole OP12a.

FIG. 7(b) schematically shows irradiation of the light L1 emitted from LED shown in FIG. 7(a) on the mask member OP12 through the optical system. The region 21e shown in FIG. 7(a) with a broken line corresponds to the shape of the through-hole OP12a shown in FIG. 7(b). As shown in FIG. 7(b), the optical system is adjusted to prevent entry of the low intensity part into the through-hole OP12a, and only the light released from the region 21e in between two electric conductor lines 22a, 22b in FIG. 7(a) selectively passes the through-hole, and therefore, the cross sectional shape of the irradiation light is formed as a rectangle.

As mentioned above, since the area between two adjacent electric conductor lines of the parallel stripe-shaped electrode is long and narrow, it preferably matches the through-hole having the rectangular section, and the light emitted from between two electric conductor lines is efficiently utilized as the irradiation light. The light emitted from between two adjacent electric conductor lines of the parallel stripe-shaped electrode has a sufficiently high light intensity, and the light characteristically shows almost uniform light intensity in the section. Therefore, the above-mentioned adverse influence on the optical particle coefficient can be sufficiently suppressed.

FIG. 4 shows one embodiment of the region 21e in between two electric conductor lines 22a, 22b adjacent to each other in the parallel stripe-shaped electrode of the LED actually utilized as the light source, wherein the region 21e is shown with a broken line. As mentioned above, the shape of the region 21e and the shape of the opening of the through-hole OP12a of the mask member OP12 correspond to each other and are similar. In the embodiment of FIG. 4, while the shape of the region 21e is rectangle, it may be square according to the shape of the opening of the through-hole.

In the embodiments of FIG. 4, FIG. 7(a) and FIG. 7(b), the longitudinal direction of the parallel electric conductor lines constituting the parallel stripe-shaped electrode of the LED is directed to be perpendicular to the flow direction of the flow channel direction of the through-hole of a mask member. However, it may be changed according to the shape of the opening of the through-hole and the like, such as being parallel to the flow direction of the flow channel and the like.

The remaining light released from the LED to the outside may be utilized for lighting and irradiation light for other optical measurement systems, by reflection by a reflection plate formed on an LED-holding part, or by dividing the light to change its optical path by various optical systems.

As shown in FIGS. 7(a) and 7(b), when only the light emitted from between two adjacent electric conductor lines of the parallel stripe-shaped electrode is utilized, the light intensity in the cross section of the light that passed through the through-hole of the mask member has high uniformity. In this case, a difference between the maximum value and the minimum value of the light intensity in the cross section of the light that passed through the through-hole can be within 10% of the maximum value.

That is, (((maximum value−minimum value)/maximum value)×100)≤10 [%].

In other words, the minimum value of the light intensity in the cross section of the light that passes through the through-hole is always not less than 90% of the maximum value, where variation of the light intensity is small and the irradiation light has high intensity. In a preferable embodiment, a difference between the maximum value and the minimum value of light intensity in the cross section of the light that passed through the through-hole can be within 5% of the maximum value and the difference can be within 1% of the maximum value in a more preferable embodiment.

The intensity of light in each part in the cross section of the light that passed through the through-hole of the mask member can be measured by inserting a light receiving element on the optical path (in the apparatus of FIG. 1, for example, between the flow cell 1 and the lens OP2 and the like). For example, in Power Meter (light output measuring device) Q8320 manufactured by Advantest Corporation, a probe extends from the main body of the measuring device, and a light receiving element is formed on the tip of the probe. The intensity of light in each part in the cross section of the light that passed through the through-hole of the mask member can also be measured using a light receiving device (light receiving device 3 in FIG. 1) formed in the particle analysis apparatus in the present invention.

The intensity of light in each part in the cross section of the light can be expressed by the intensity of signals output from the light emitting element used for the measurement relative to the center wavelength of the irradiation light to be measured (relative intensity (arbitrary unit)).

The particle to be analysis target in the present invention is not particularly limited and may be, for example, a fine particle, liposome and the like enclosing a drug, and the like. When blood cells such as red blood cell, white blood cell, platelet and the like are the analysis (counting, classifying and the like) target, the apparatus of the present invention which is compact due to the use of LED as a light source is remarkably useful in medical sites and inspection institute and the like.

The width of the flow channel when blood cells are the analysis target is about 10 µm-1000 µm, and the length of the irradiation segment is about 10 µm-2000 µm. The ratio of the width of the flow channel and the length of the irradiation segment is not particularly limited, and the ratio of conventionally-known particle analysis apparatuses. In consideration of the ratio, and by further adding margin of the width direction of the flow channel, the ratio of each side of the opening of the through-hole can be determined.

Examples of the items to be analyzed when blood cells are the analysis target include classification of blood cells, count thereof per kind and the like based on simple count of the blood cells, count of the blood cells per volume, absorbance and the like.

When blood cells are analyzed, the prior art can be referred to as for the sample solution and sheath liquid, showing in graph (frequency distribution graph and scattergram) of particle count results by flow cytometry, analysis method, data treatment method and the like.

For example, for classification of white blood cells into 5 types (classification into lymphocyte, monocyte, neutrophil, eosinophils, basophil) and counting of each blood cell, a sample solution is prepared by treating the whole blood by hemolysis, dilution, staining, and the volume and absorbance of each blood cell are measured by flow cytometry by the present apparatus therefor. The measurement data (volume, absorbance) obtained for each blood cell is plotted, for example, on an X-Y flat plane consisting of the X-axis (horizontal axis of volume) and the Y-axis (vertical axis of absorbance), whereby a scattergram showing how much volume of blood cells is present at how much density can be obtained. Such scattergram preferably shows distribution of each of lymphocyte, monocyte, neutrophil, eosinophil, basophil.

The particle analysis apparatus of the present invention may have electrodes provided in the flow channel so that not only particle analysis based on flow cytometry but also particle analysis based on the impedance method can be performed.

According to the present invention, the problem of the halogen lamp can be solved, and the particle analysis apparatus having the down-sized light source can be provided while ensuring the irradiation light with sufficient intensity on the irradiation segment of the flow channel. In addition, the uniform light having the sufficient intensity can be irradiated in the irradiation region even by using the LED as the light source.

This application is based on patent application No. 2014-147744 filed in Japan, the contents of which are incorporated in full herein.

The invention claimed is:

1. A particle analysis apparatus comprising a configuration to analyze particles in a sample solution based at least on flow cytometry, the particle analysis apparatus comprising:
   a flow cell having a flow channel for flowing a sample solution comprising particles to be analyzed;
   a light source device for emitting an irradiation light for said flow cytometry;
   an optical system for irradiating the irradiation light on an irradiation segment in the flow channel; and
   a light receiving device for detecting the light obtained by irradiating the irradiation light on the irradiation segment;
wherein
   the light source device comprises a light emitting diode as a light source, the light emitting diode including an electrode covering a light extraction surface of the light emitting diode, the electrode comprising a plurality of electric conductor lines arranged in parallel to each other on the light extraction surface to prevent covered portions of the light extraction surface covered by the electrode from emitting the irradiation light, portions of the light extraction surface which the electrode does not cover comprising uncovered portions of the light extraction surface configured to emit the irradiation light;
   the covered portions and the uncovered portions are arranged on the light extraction surface in a pattern such that the irradiation light forms a plurality of alternating high intensity parts and low intensity parts on a surface of the flow cell, the plurality of alternating high intensity parts and low intensity parts being parallel to each other and perpendicular to a flow direction of the flow channel of the flow cell, the flow sequentially passing through the plurality of alternating high intensity parts and low intensity parts of the irradiation light;

a longitudinal direction of the plurality of electric conductor lines arranged in parallel to each other, which are contained in the electrode of the light emitting diode, is perpendicular to the flow direction of the flow channel of the flow cell;

the optical system further comprises a mask member positioned between the flow channel and the light source device, the mask member having a through-hole to form a cross sectional shape of the irradiation light;

a length of a long side of the cross sectional shape of the irradiation light irradiated on the flow channel is longer than a width of the flow channel; and the flow direction is a lengthwise direction of the flow channel.

2. The particle analysis apparatus according to claim 1, wherein the mask member is positioned such that, from among the lights emitted from the light emitting diode, only a light emitted from between two adjacent electric conductor lines selected from the plurality of electric conductor lines contained in the electrode passes through the through-hole of the mask member and is irradiated on the irradiation segment.

3. The particle analysis apparatus according to claim 2, wherein a difference between a maximum value and a minimum value of light intensity in a cross section of a light that passes through the through-hole of the mask member is within 10% of the maximum value.

4. The particle analysis apparatus according to claim 1, wherein the particles are blood cells, and the particle analysis apparatus comprises a configuration to count the blood cells based at least on flow cytometry.

5. The particle analysis apparatus according to claim 1, wherein the through-hole of the mask member has a rectangular opening shape, and a direction of a long side of the rectangular opening shape is perpendicular to the flow direction and the same as the longitudinal direction of the plurality of electric conductor lines arranged in parallel to each other, which are contained in the electrode of the light emitting diode.

6. The particle analysis apparatus according to claim 5, wherein a difference between a maximum value and a minimum value of light intensity in a cross section of a light that passes through the through-hole of the mask member is within 10% of the maximum value.

* * * * *